United States Patent [19]

Russek

[11] 4,432,368

[45] Feb. 21, 1984

[54] AUTOMATIC ELECTRODE PLACEMENT DEVICE

[75] Inventor: Allen S. Russek, Medford, N.Y.

[73] Assignee: Wallant International Trade, Inc., New York, N.Y.

[21] Appl. No.: 277,940

[22] Filed: Jun. 26, 1981

Related U.S. Application Data

[63] Continuation-in-part of Ser. No. 190,242, Sep. 24, 1980, Pat. No. 4,381,012.

[51] Int. Cl.³ .............................................. A61B 5/04
[52] U.S. Cl. .................................... 128/644; 128/802
[58] Field of Search ........ 128/639, 644, 783, 791–793, 128/798, 799, 802

[56] References Cited

U.S. PATENT DOCUMENTS

| | | | |
|---|---|---|---|
| 3,409,007 | 11/1968 | Fuller | 128/644 |
| 3,534,727 | 10/1970 | Roman | 128/644 |
| 3,612,061 | 10/1971 | Collins et al. | 128/799 |
| 3,888,240 | 6/1975 | Reinhold, Jr. et al. | 128/644 |
| 3,971,387 | 7/1976 | Mantell | 128/792 |
| 3,998,213 | 12/1976 | Price | 128/644 |
| 4,121,575 | 10/1978 | Mills et al. | 128/644 |
| 4,202,344 | 5/1980 | Mills et al. | 128/644 |

OTHER PUBLICATIONS

Petrucelli et al., "A Seriel to Parallel . . . Tens Pain Suppression", Proceedings of 7th N.E. Conf., 22-23 Mar. 1979 pp. 388-390.

Tens-Pac, Instructions for use, Model D, Catalog no. 1010-0001 Transcutaneous Electrical Nerve Stimulator, Dow Corning Wright.

Primary Examiner—Lee S. Cohen
Attorney, Agent, or Firm—Frishauf, Holtz, Goodman and Woodward

[57] ABSTRACT

A device for placement against a body and for loacting at least one electrode at predetermined portions of a body includes a first portion having at least one electrode thereon, said at least one electrode overlying at least two stimulation points on the body of a wearer, and electrical connectors coupled to the first portion for electrically connecting the at least one electrode to an electrical signal receiving and/or generating device. The device is removably secured to the body of a wearer with a predetermined automatic orientation relative to the body of a wearer so that the at least one electrode is properly located adjacent a body portion of the wearer to overlie said at least two stimulation points. A locating device is provided on the device for positively placing the device relative to a predetermined body portion of the wearer to insure proper electrode placement against the body.

11 Claims, 14 Drawing Figures

AUTOMATIC ELECTRODE PLACEMENT DEVICE

CROSS REFERENCE TO RELATED APPLICATION

This is a continuation-in-part of Ser. No. 190,242, filed Sept. 24, 1980, now U.S. Pat. No. 4,381,012 the entire contents of which are incorporated herein by reference.

BACKGROUND OF THE INVENTION

This invention relates to an automatic electrode placement device for automatically placing and securing electrodes for transcutaneous nerve stimulation, monitoring of body functions, etc. at predetermined sites, such as sites located over or near a nerve root or dermatome.

At present, transcutaneous nerve stimulation (hereinafter referred to as TENS) to relieve pain is carried out by placing electrodes on specific body portions of the patient. The precise locations of the electrodes is critical for best results. When using a TENS device in connection with management of pain, it is time consuming and difficult for a practitioner to locate the electrodes at proper points on the patient to provide the desired pain relieving results. Moreover, after the patient leaves the practitioner's office, and takes the TENS device home, it is extremely difficult for the patient, using present-day devices and electrodes, to locate by himself the correct locations for placement of the electrodes to provide best pain relieving results. Particular considerations apply with respect to the shoulder, neck, upper and lower back areas and other areas of the body which are neither visible nor normally accessible for self placement of the electrodes, especially for people who are in pain and who may have limited body movement capabilities.

The term "electrode" is used herein to describe an "electrical conduction means" for applying electrical stimulation to a body or for receiving electrical signals from the body when it is in contact with a body portion. Any type of electrical conduction device can be used as an electrode, as desired.

It is extremely difficult for the patient to secure the electrodes at the proper location sites. Current practice is to utilize adhesive tape patches over the electrodes, adhesive coated electrodes or strips of adhering paper using 3M adhesive preparations trademarked Dermacil and Micropore ® which adhere to the skin. The electrodes must be secured for many hours since the devices are used intermittently throughout the day and transported by the patient connected to the body. Suction cup and other self adhering electrodes will not remain attached to the body for necessary time periods. When using TENS and related electronic devices, the patient is cautioned against continued use if skin rash or irritation is caused by the adhesive. The present invention eliminates the need for adhesives and possible side effects from their usage.

In some cases, it is difficult for the practitioner to even find the proper locations for placement of the electrodes on the patient's body. The present invention has been designed to obviate or reduce this difficulty.

While the above description is given with respect to TENS devices, similar considerations also apply for various other electronic devices requiring electrode placement at specific body locations. Throughout the following specification, only TENS devices will be discussed, it being apparent that various other electronic devices which require electrode placement on the body are within the scope of this disclosure.

The object of the present invention is to provide a device which permits automatic accurate and easy location of electrodes on the body of the patient for use with, for example, TENS devices or other electronic devices requiring continuously secure and accurate electrode placement against the body of a patient. It is also an object that the patient can repeatedly achieve such accurate electrode placement after leaving the practitioner's office.

A further object of the invention is to provide such a device which enables electrodes to be accurately located at specific body locations in a simple, repeatable and expedient manner.

A further object of the invention is to provide such a device which enables a great variety of electronic stimulation points to be selected so that the device may be used for multiple purposes.

Yet another object of the invention is to provide such a device which is simple in construction reliable, long lasting easily adjustable and which may be laundered or otherwise cleaned so as to keep it in a sanitary condition. It may be made of one or more parts which may be easily detached from each other.

Still another object is to provide an automatic electrode placement device with electrodes mounted at fixed points and which will provide proper electrode placement for virtually all adults, regardless of size or weight, thereby eliminating the requirement of determining electrode placement for each individual being treated.

SUMMARY OF THE INVENTION

A device for continuously fixed automatic anatomically correct placement of at least two electrodes against a plurality of predetermined areas of a body, comprises: a first portion adapted to be placed against a body portion of a wearer, the first portion having at least two electrodes for overlying the plurality of predetermined body areas; means for electrically connecting the electrodes to an electrical signal generating and/or signal receiving device; means for removably securing the device to the body of the wearer with the at least one electrode adjacent to the one or more predetermined body portions of the wearer; and locating means thereon for positively and automatically locating the device relative to a given body portion of a wearer such that said electrodes overlie the predetermined body areas. In a preferred arrangement, the locating means comprises means for locating and abutting the sacrococcygeal joint of a wearer, the location of the points overlied by the electrodes being related to the sacrococcygeal joint of the wearer.

DETAILED DESCRIPTION

Figures 1, 1A, 2, 3:
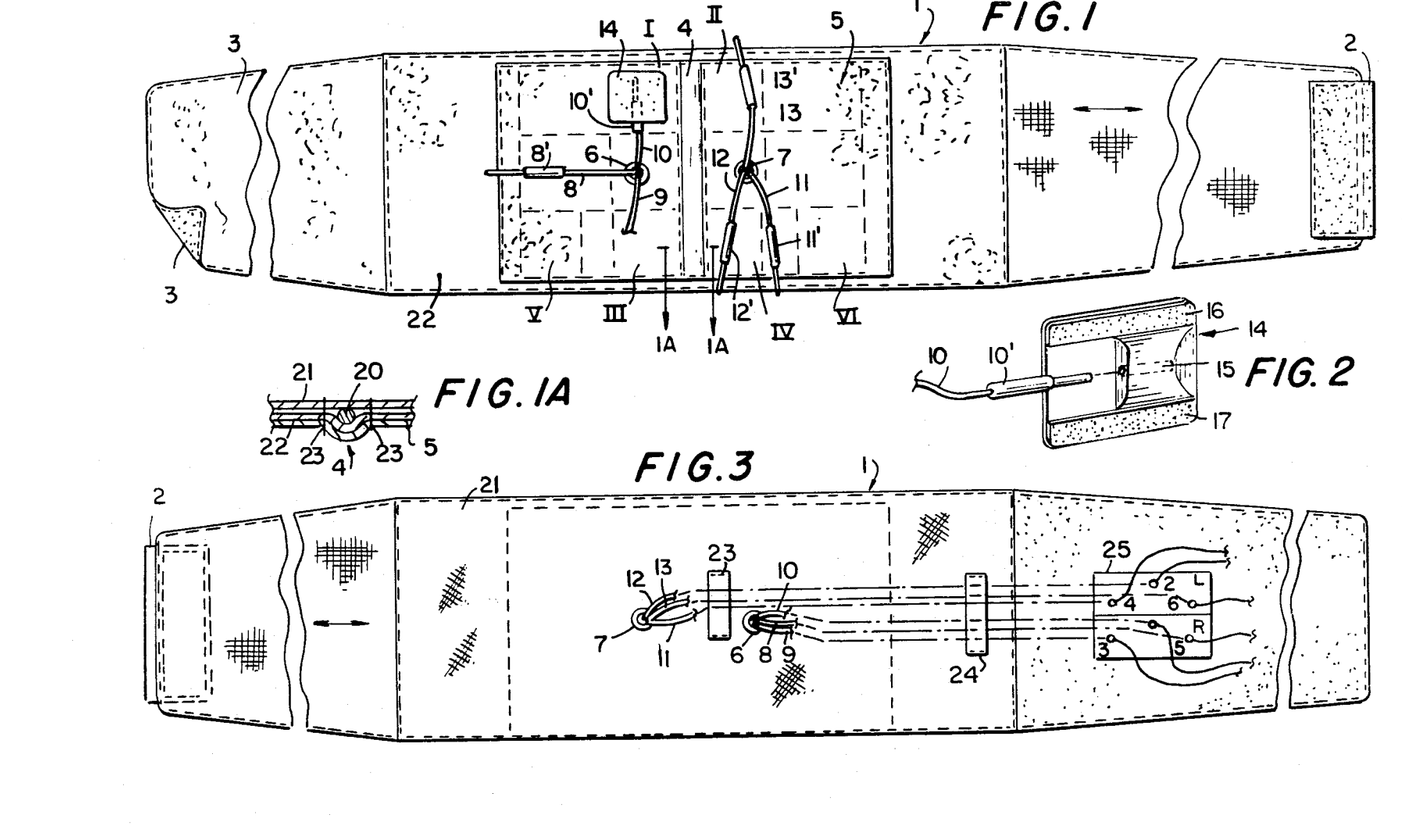
FIG. 1 is a view of the inside portion of a belt-like device for use in locating electrodes in the vicinity of the lower back.
FIG. 1A is an exploded sectional view of the portion designated 1A—1A in FIG. 1.
FIG. 2 is an exploded view of a typical electrode for use with the device of FIG. 1.
FIG. 3 is an outside view of the device of FIG. 1.

Referring to FIGS. 1-3, a belt-like electrode placement device 1 disclosed in Ser. No. 190,242, is made of a fabric which is preferably washable and/or dry cleanable. Secured at one end of the fabric is a hook-type Velcro connector 2, the hooks of which face inwardly of the garment. At the other end of the garment is a loop-type Velcro fastener material 3, on the outer side of the garment, for adjustable connection with the hook-type Velcro fastener portion 2.

Located centrally of the device is a locator portion 4 which may be a stiffened and/or protruding portion as shown in FIG. 1A. This locating portion 4 is provided so that the patient may align same with, for example, the spine, thereby insuring that the device is properly located on the body of the patient each time it is used, so that electrode placement will be consistently repeatable. Locating portion 4 in FIGS. 1 and 1A comprises a fabric or other filler member 20 located between layers 21, 22 of the belt, seams 23 keeping the members in relative position. The locating portion 4 may protrude inwardly (FIG. 1A) and/or outwardly of the device. Locating portion 4 may instead comprise a rough, but non-irritating fabric portion or layer which is placed and located against, for example, the spine. In this case it is not necessary for portion 4 to protrude.

The central inner portion of the device includes a further loop-type Velcro fastening area 5 on which electrodes are to be placed at various specified locations. The drawing illustrates six locations I-VI. It should be clear that more or fewer specified electrode placement locations could be provided, six being shown merely by way of example. The six locating areas are preferably visually designated on the Velcro area 5, for example by imprinting or other technique, so that the patient and physician will be able to precisely locate the electrodes thereon. The indicated electrode locations apply to substantially all or most body configurations. Alternatively, the Velcro portion 5 may be provided in a blank state, the physician outlining or marking the specified electrode locations, for example with a marking pen, or the like, after the specific locations for a given patient have been determined. This need only rarely be done since the pre-indicated locations are correct for almost all people. The six locations are generally used in pairs, two cooperating electrodes being used in respective pairs. For example, two electrodes placed at respective locations I and II may constitute a pair, electrodes at respective locations III and IV may constitute a pair, etc. For dual channel TENS devices, two pairs of electrodes may be simultaneously used.

The belt of FIG. 1 has electrical wires 8–13 extending therethrough, between fabric layers 21,22, the electrical wires extending out in FIG. 1 through grommets 6,7. Other techniques for passing the wires through the belt could be used, as desired and as expedient in specific applications. The wires 8–13 each have respective plugs 8'–13' at the ends therefor for connection with electrodes such as electrode 14 which is shown in greater detail in FIG. 2. Electrode 14 is a conventional type of electrode made of electroconductive flexible preferably rubber-like material and having a receptacle 15 therein for receiving a plug such as plug 10' as shown in FIG. 2. Electrodes of the type generally shown in FIGS. 1 and 2 are designated in the trade as, for example, flexible carbon electrodes. Such electrodes are from, for example, Uni-Patch Inc., Wabash, Minn. The electrode 14 also has hook-type Velcro fasteners 16,17 on the rear surface thereof for adjustable engagement with the loop-type Velcro surface 5 so that it may be adjustably placed any way on surface 5. Fasteners 16,17 may be sewn onto electrodes 14, or may be attached by an appropriate adhesive. Any desired number of electrodes 14 may be used, depending upon the treatment desired and the capacity of the electronic device, such as a TENS device, to which the electrodes are connected. Only one electrode 14 is illustrated in FIG. 1 for ease of illustration.

As shown in FIG. 3, the wires 8–13 pass through the grommets 6,7 and extend between the fabric layers 21,22 of the device. Wire locating loops 23,24, which are preferably pieces of fabric stitched to one or the other of fabric layers 21,22 are provided to guide the wires 8–13 toward the end portion of the belt. The wires 8–13 extend to a plate 25 and pass therethrough so as to be fed to an electronic device, such as a TENS device. The plate 25 has left (L) and right (R) designations thereon, and also includes numberings for the various wires so that they may be easily identified for connection to the electronic input device. Details of how the wires 8–13 are connected to the electronic device such as a TENS device, are omitted since they are readily apparent to those skilled in the art to which the present invention pertains.

Figure 4:
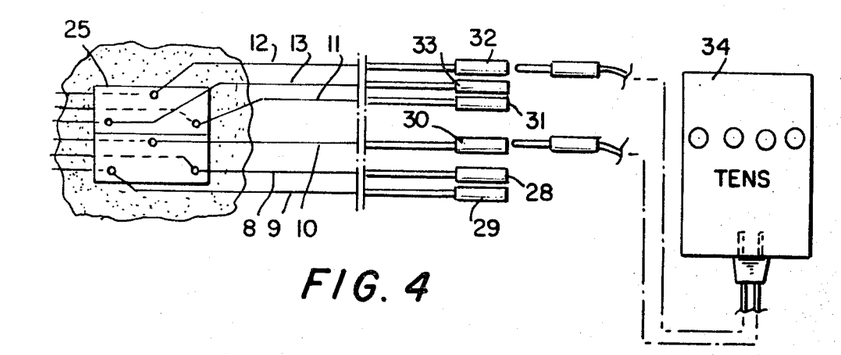
FIG. 4 is a partial exploded view of the connector portion of FIGS. 1 and 3, showing the device connected to a TENS device.

FIG. 4 illustrates how the wires 8–13 extend from the plate 25 and, in the illustrated embodiment, have sockets or receptacles 28–33, respectively at the ends thereof for connection to plugs of an electronic device, such as a TENS device 34 for energization of electrodes of the belt-like device. The TENS device 34 is shown with only two electrical wires extending therefrom. However, a dual channel device having four wires can be used, as desired.

Figure 5:
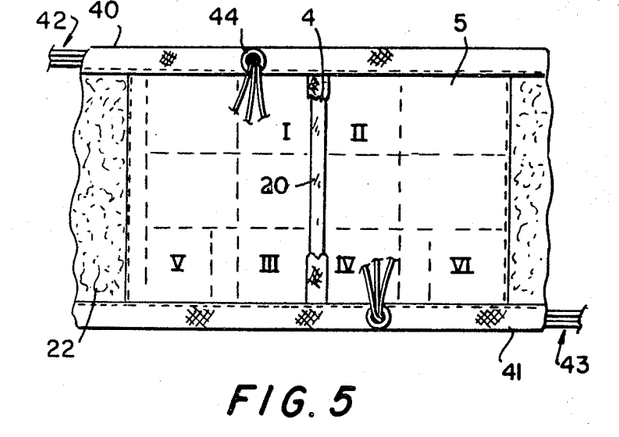
FIG. 5 is a partial inner view of a modified device.

FIG. 5 illustrates a modified device having a loop-like seamed arrangement 40, 41 between the fabric layers so as to provide a channel through which wires generally designated 42, 43 may pass for connection between an electronic device and electrodes. The wires preferably pass through a grommet 44 or other opening in the passageways or channels 40, 41.

Figure 6:
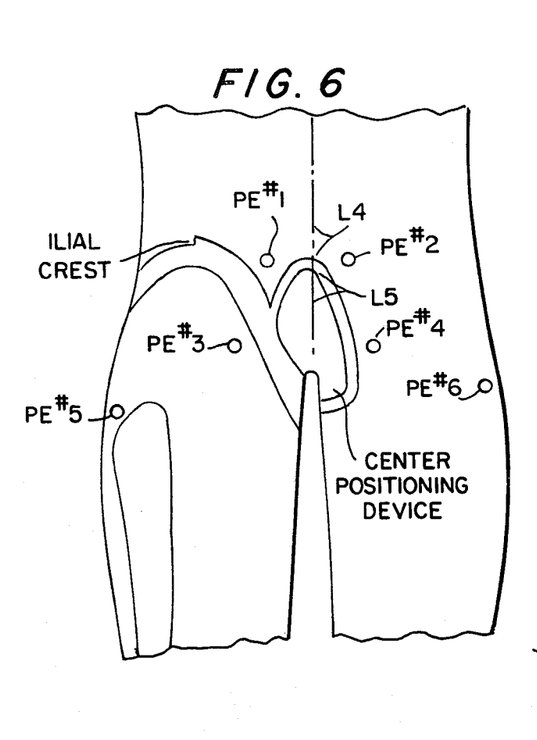
FIG. 6 is a rear view of the lower back portion of a person showing the anatomical locations for predetermined electrode placement for TENS stimulation.

FIG. 6 is an illustration of the rear portion of the human body with six anatomical locations for predetermined electrode placement for carrying out TENS stimulation. It has been unexpectedly discovered that these points are substantially the same for virtually every adult patient, regardless of the size or weight of the adult. If electrodes of sufficient size are located at the relative points illustrated in FIG. 6, they will occupy a stimulating proximity to the desired nerve roots or dermatomes, regardless of the size or weight of the adult patient, since stimulation will be directed to the course of these nerve roots and dermatomes rather than to the electrode centering points. By providing electrodes with centering points at substantially the points indicated in FIG. 6, such an unexpected result will be obtained. The points E1-E6 illustrated in FIG. 6 can be defined relative to the sacro-coccygeal joint (see center positioning device in FIG. 6) and/or the iliac crest.

Figure 7:
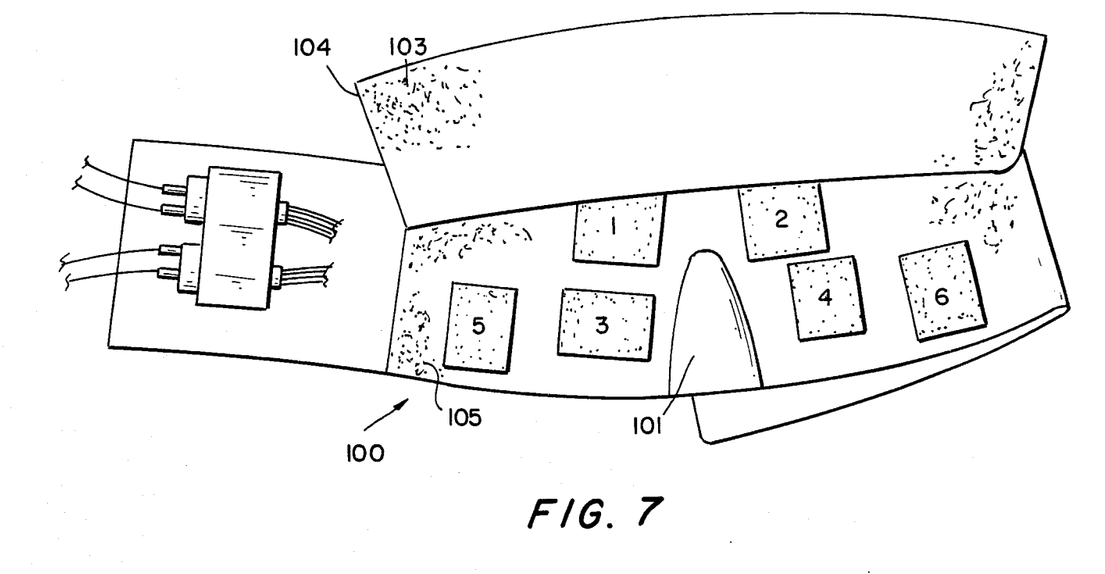
FIG. 7 illustrates a belt arrangement for locating the electrodes at the predetermined electrode placement points shown in FIG. 6.
Figure 8:
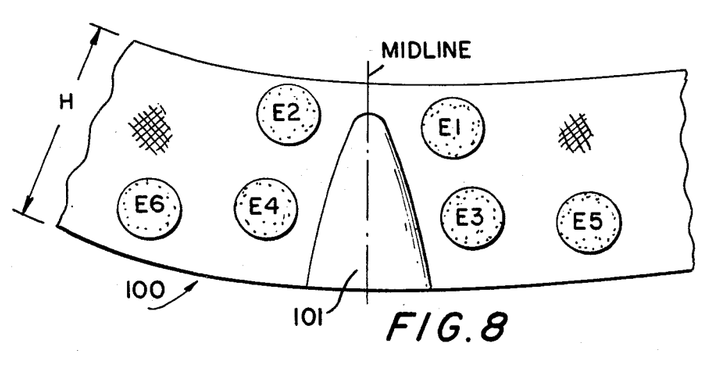
FIG. 8 illustrates a locating device of FIG. 7 in greater detail.
Figure 9:
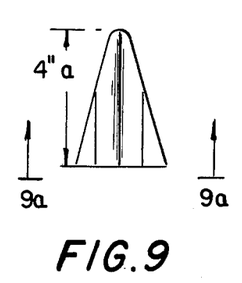
FIGS. 9,9a and 9b illustrate, respectively, top, end and side views of a sacro-coccygeal centering device of the invention.
Figure 9A:
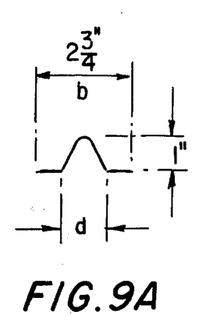
Figure 9B:
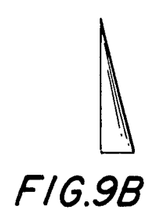

FIGS. 7 and 8 illustrate a belt in accordance with the present invention for locating electrodes at specific points to cover the points indicated in FIG. 6. FIG. 9 illustrates the locating device for the sacro-coccygeal joint in greater detail.

In the embodiment of FIGS. 7 and 8, the points of reference are the mid-line of the spine of the person and the prominence of the sacro-coccygeal joint. In order to achieve such centering, a molded plastic member of the shape generally shown in FIG. 9 is inserted into a pocket 101 formed in the belt 100. The pocket is formed by, for example, stitching a second member over the belt 100 to form a receiving area for the plastic member shown in FIG. 9. This member protrudes and the patient can feel it as it settles into the gluteal cleft and covers the prominence of the sacro-coccygeal joint. If desired, the centering member shown in FIG. 9 can be formed of a heat deformable material so that the practitioner can precisely mold it to fit each individual patient.

In a preferred arrangement, each electrode E1-E6 illustrated in FIG. 8 has a diameter of about two inches and is so placed that electrodes E1 and E2 will overlay the course of nerve roots as they emerge from between the vertebrae. Electrodes E3 and E4 are arranged so that they will overlay nerve roots over the lateral borders of the sacrum. Electrodes E5 and E6 are arranged so that they will rest on dermatomes. Preferably, the electrodes are round and are one (1) to two (2) inches in diameter. Other sizes may of course be used, and other shapes may be used, such as oval, rectangular, etc.

Relative to the points of reference:

Electrodes E1 and E2 will be centered 2¼ inches from the midline (spine), horizontally, and 4¼ inches above the sacro-coccygeal joint.

On a horizontal plane, electrodes E1 and E2 will be 4¼ inches apart.

Electrodes E3 and E4 will be centered 3¼ inches from the midline, horizontally, and 2¼ inches above the sacro-coccygeal joint, vertically.

On a horizontal plane, electrodes E3 and E4 will be 6½ inches apart.

Electrodes E5 and E6 will be centered 6¾ inches from the midline, horizontally, and ⅞ths of an inch above the sacro-coccygeal joint, vertically.

On a horizontal plane, electrodes E5 and E6 will be 13½ inches apart. It is emphasized that each electrode E1-E6 has a sufficient radius to occupy a stimulating proximity to the desired nerve roots or dermatomes regardless of the size or weight of the adult patient, since stimulation will be directed to the course of these nerve roots and dermatomes rather than to the electrode centering points. If the patient is sensitive to intense electrical stimulation, the electrodes could be made larger to overlie a longer course of the nerve in question to disperse the total electrical stimulation over a larger area.

When electrodes are arranged as set forth above, it has been discovered that pain relieving effects using a TENS stimulator can be achieved for virtually all adults, regardless of size or weight, using the belt of the present invention, without requiring specific and tailored electrode locating procedures by the practitioner or by the patient.

As shown in FIG. 7, the rear or outside portion of the belt is covered with a flap 103 using Velcro fasteners 104,105 to cover the outside of the belt to provide a finished appearance. The inside, or body side of the belt is as shown in FIG. 8.

Figure 10:
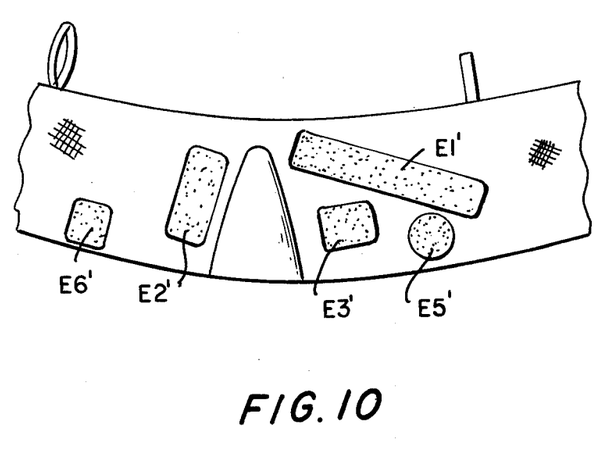
FIG. 10 illustrates a modification of the invention.

FIG. 10 illustrates a further modification of the invention comprising only four electrodes. In FIG. 10, electrode E6' corresponds to electrode E6 of FIG. 8; electrode E3' corresponds to electrode E3 of FIG. 8; and electrode E5' corresponds to electrode E5 in FIG. 8. Electrode E2' combines the functioning of electrodes E2 and E4 of FIG. 8, and electrode E1' of FIG. 10 replaces electrode E1, and further stimulates additional points. In the embodiment of FIG. 10, electrode E2' covers the points covered by the electrodes E2 and E4 of FIG. 8. In this embodiment, it is necessary that the TENS drive device have sufficient power to provide a sufficient signal to stimulate the desired points (E2 and E4 in FIG. 6) using such a large electrode. Electrode E1' is large enough to cover dermatomes in the course of the nerve passing through point PE1 (FIG. 6).

Figure 11:
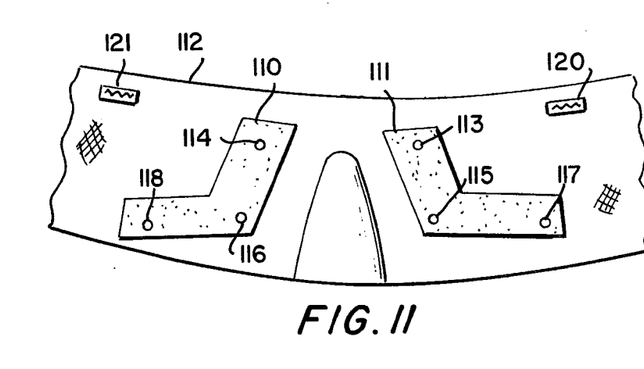
FIG. 11 illustrates yet another modification of the invention.

FIG. 11 illustrates yet another embodiment of the invention having large generally L-shaped electrodes 110,111 which may be mounted to the belt 112 in a manner similar to the previously described embodiments. The electrodes 110,111 are large enough to cover the stimulation points 113-118 which correspond to the points E1-E6 in FIG. 6. In this embodiment, sufficient electrical stimulation is applied to the electrodes 110,111 to provide a sufficient effect over the points 113-118, thereby providing an even more simple overall structural arrangement.

Referring again to the embodiment illustrated in FIG. 8, it is again noted that the center points of each of the electrodes E1-E6 are arranged so as to fall over the points E1-E6, respectively, in FIG. 6. Since the electrodes are larger than the points of stimulation in FIG. 6, if there is any slight error in location of the electrodes, or variation of location of the points in any particular person to some slight degree, sufficient coverage is obtained. The center points of electrodes E1 and E2, when located 4¼ inches above the sacro-coccygeal joint, will also be about ½ inch below the highest level of the posterior iliac crest. Electrodes E3 and E4, when located 2½ inches above the sacro-coccygeal joint will be about 3¼ inches below the highest level of the posterior iliac crest. The centerpoints of electrodes E5 and E6, when located ⅞ths of an inch above the sacro-coccygeal joint will be about 4⅛ inches below the highest level of the posterior iliac crest. When the center positioning device shown in FIGS. 8, 10 and 11 is located in position on the body, the various electrodes will all be in the desired predetermined positions to stimulate the desired nerves.

In a preferred arrangement, the height of the belt (I mention H in FIG. 8) is preferably 6 inches. With such a belt dimension, the following dimensions apply:

Electrodes E1 and E2—1½" from the top of belt; 2½" from the mid-line of belt.

Electrodes E3 and E4—2½" from the bottom of belt; 3¼" from the mid-line of belt.

Electrodes E5 and E6—1½" from the bottom of belt; 6¾" from the mid-line of belt.

Distance from E1 To E2=4¼ inches
Distance from E3 to E4=6½ inches
Distance from E5 to E6=13½ inches
All points refer to the center of the electrode.

It should be clear that various size electrodes could be used. While 2 inch diameter electrodes have been found to provide excellent results, larger or smaller electrodes, rectangular or square electrodes, or other shaped electrodes could be used, as desired.

In a preferred embodiment, the sacro-coccygeal centering and locating device illustrated in FIG. 9 has dimensions as follows:
 a=4 inches, approximately
 b=2¾ inches, approximately
 c=1 inch, approximately
 d=1¾ inches, approximately.

It should be clear that the belt of the present invention may have the spinal locating member 4 in FIG. 1 in addition to the sacro-coccygeal joint locating member of FIG. 9. Alternatively, or in addition to the other locating devices, an iliac crest locating device can be provided, such as shown in FIG. 11. As shown in FIG. 11, locating elements 120,121 can be provided on the inner surface of the belt and/or on the outer surface of the belt so that the wearer can locate these members at the iliac crest. The locating members can either be different colored areas which the wearer will press on with his fingers and locate them at the iliac crest, or they may be rough or otherwise textured patches or elements on the belt which can be felt by the wearer when locating the belt with these members at the iliac crest to properly locate same. It has been found in practice that the sacro-coccygeal joint locating device of FIG. 9 is easier and more convenient to use.

While the above embodiments are described with electrodes arranged to contact body portions on both sides of the spinal column, if desired, electrodes can be provided on only one side of the spinal column. Additionally, if electrodes are provided on only one side of the spinal column, the three electrodes illustrated in FIG. 6 can be replaced by a single electrode as shown in FIG. 11, or by one or more larger electrodes which cover one or more stimulation points, such as shown in FIG. 10. Alternatively, it is possible to provide the device of the present invention, with the unique locating means, with one or more electrodes arranged to contact one or more respective stimulation points, such as the points shown in FIG. 6.

Still further, while the invention is described with respect to a belt-like embodiment, other arrangements could be provided, such as a panel which has the sacro-coccygeal centering and locating device, but which is not arranged as a belt. Such a device could, for example, be otherwise strapped to the body, or taped to the body.

An interesting feature of the present invention is that the points PE1–PE6 illustrated in FIG. 6 of the drawings are effective points which overlie the most superficial or accessible portions of the deeper nerves, requiring the least amount of "penetration" or resistance to overcome. The superficial and deep nerves can be more heavily loaded with electrical stimuli than the cutaneous terminal filaments and will not have a tendency to "adapt" as readily, blocking pain in the spinothalamic tract. This is important, since the technique used in connection with the structure of the present invention should impart intense bombardment of electrical impulses and excitation of the peripheral nerves without evoking a strong nociceptor reaction. As mentioned above, any or all of the electrode points EP1–EP6 can be stimulated, depending upon the desired effect. In some cases, one or more stimuli points can be more effective than others. This can be determined by the practitioner by trial and error.

I claim:

1. A device for continuously fixed automatic anatomically correct placement of at least one electrode means against one or more predetermined portions of a body, said at least one electrode means being adapted to transmit electrical signals, said device comprising:
   a substantially non-stretchable first portion adapted to be placed against a body portion of a wearer, said first portion having at least one electrode means at at least one electrode receiving position thereon;
   means for electrically connecting said at least one electrode means to an electrical signal generating and/or signal receiving device;
   touch-type locating means on said first portion and being cooperable with a given body portion of a wearer, said given body portion of the wearer having touch locatable characteristics, for positively automatically locating said device relative to said given body portion of the wearer, said at least one electrode means being a corresponding substantially fixed distance from said locating means so as to be adjacent said one or more predetermined body portions of the wearer each and every time the device is mounted to the body of the wearer, said one or more predetermined body portions being substantially fixed distances from said given body portion which last mentioned fixed distances are substantially the same as respective first mentioned fixed distances; and
   means for removably securing said first portion to the body of the wearer with said touch-type locating means adjacent said given body portion of the wearer and with said at least one electrode means adjacent to said one or more predetermined body portions of the wearer;
   said locating means comprising means for locating and abutting the sacro-coccygeal joint of a wearer.

2. The device of claim 1 comprising at least two of said electrode means, each of which is adapted to be placed against a respective predetermined body area of the wearer which is located at or near a nerve root of the body.

3. The device of claim 1, further comprising a plurality of said electrode means, each of which is mountable to said first portion so as to overlie at least one predetermined body area which is located at or near a nerve root of the body of the wearer.

4. The device of claim 1, wherein said locating means comprises a generally triangular member having a raised portion thereon for abutting the sacro-coccygeal joint of the wearer.

5. The device of claim 1, wherein said electrode means overlie at least points PE1–PE4 on said device with the following locations relative to the sacro-coccygeal joint locating means;
   points PE1 and PE2 will be centered about 2⅛ inches from around the midline (spine), horizontally and about 4¼ inches above the sacro-coccygeal joint locating means;
   on a horizontal plane, points PE1 and PE2 will be about 4¼ inches apart;

points PE3 and PE4 will be centered about 3¼ inches from around the midline, horizontally, and about 2¼ inches above the sacro-coccygeal joint locating means, vertically; and on a horizontal plane, points PE3 and PE4 will be about 6½ inches apart.

6. A device for continuously fixed automatic anatomically correct placement of at least one electrode means against one or more predetermined portions of a body, said at least one electrode means being adapted to transmit electrical signals, said device comprising:

a substantially non-stretchable first portion adapted to be placed against a body portion of a wearer, said first portion having at least one electrode means at at least one electrode receiving position thereon;

means for electrically connecting said at least one electrode means to an electrical signal generating and/or signal receiving device;

touch-type locating means on said first portion and being cooperable with a given body portion of a wearer, said given body portion of the wearer having touch locatable characteristics, for positively automatically locating said device relative to said given body portion of the wearer, said at least one electrode means being a corresponding substantially fixed distance from said locating means so as to be adjacent said one or more predetermined body portions of the wearer each and every time the device is mounted to the body of the wearer, said one or more predetermined body portions being substantially fixed distances from said given body portion which last mentioned fixed distances are substantially the same as respective first mentioned fixed distances; and means for removably securing said first portion to the body of the wearer with said touch-type locating means adjacent said given body portion of the wearer and with said at least one electrode means adjacent to said one or more predetermined body portions of the wearer;

said locating means comprising means for locating said first portion such that said at least one electrode means is located vertically between the midline of the spine and a pain site on the wearer, and horizontally directed toward the outer body areas of the wearer or to the upper muscular skeletal body section of the wearer.

7. A device for continuously fixed automatic anatomically correct placement of at least one electrode means against one or more predetermined portions of a body, said at least one electrode means being adapted to transmit electrical signals, said device comprising:

a substantially non-stretchable first portion adapted to be placed against a body portion of a wearer, said first portion having at least one electrode means at at least one electrode receiving position thereon;

means for electrically connecting said at least one electrode means to an electrical signal generating and/or signal receiving device;

touch-type locating means on said first portion and being cooperable with a given body portion of a wearer, said given body portion of the wearer having touch locatable characteristics, for positively automatically locating said device relative to said given body portion of the wearer, said at least one electrode means being a corresponding substantially fixed distance from said locating means so as to be adjacent said one or more predetermined body portions of the wearer each and every time the device is mounted to the body of the wearer, said one or more predetermined body portions being substantially fixed distances from said given body portion which last mentioned fixed distances are substantially the same as respective first mentioned fixed distances; and means for removably securing said first portion to the body of the wearer with said touch-type locating means adjacent said given body portion of the wearer and with said at least one electrode means adjacent to said one or more predetermined body portions of the wearer;

said locating means comprising means on said device for positively and automatically locating and abutting at least one iliac crest of the wearer.

8. The device of claim 7, wherein said locating means comprises sensing means on said device for creating a sensual feeling to the wearer when located against the body of the wearer to facilitate location and orientation with respect to the iliac crest of the wearer.

9. The device of any one of claims 1, 6 or 7, wherein said at least one electrode means comprises at least one electrode having a predetermined shape and size for distributing the energy of an electrical signal to a predetermined area of the body of the wearer.

10. The device of any one of claims 1, 6 or 7, wherein said first portion comprises a belt-like member which includes means for opening and closing same for removal and attachment from and to the body of a wearer.

11. The device of claim 10, wherein said belt-like member is at least partially of elastic material for secure maintenance of the first portion with respect to the body of the wearer.

* * * * *